US00PP13298P3

(12) United States Plant Patent
Griesbach et al.

(10) Patent No.: US PP13,298 P3
(45) Date of Patent: Dec. 3, 2002

(54) ORNITHOGALUM PLANT NAMED 'CHESAPEAKE SUNBURST'

(75) Inventors: Robert Griesbach, Ellicott City, MD (US); Fred Meyer, deceased, late of Escondido, CA (US), by Marlene Meyer, administrator

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 09/765,318

(22) Filed: Jan. 22, 2001

(65) Prior Publication Data

US 2002/0100090 P1 Jul. 25, 2002

(51) Int. Cl.[7] ..... A01H 5/00
(52) U.S. Cl. ..... Plt./263

(58) Field of Search ..... Plt./263

(56) References Cited

PUBLICATIONS

U.S. National Arboretum Plant Introduction, Floral and Nursery Plants Research Unit, Ornithogalum 'Chesapeake Blaze', 'Chesapeake Sunburst', and 'Chesapeake Sunset', Nov. 1999.*

* cited by examiner

*Primary Examiner*—Bruce R. Campell
*Assistant Examiner*—June Hwu
(74) *Attorney, Agent, or Firm*—C. A. Whealy

(57) ABSTRACT

A new and distinct cultivar of Ornithogalum plant named 'Chesapeake Sunburst' characterized by its strong and upright scapes; dense corymbose racemes with numerous bright yellow-colored flowers; and glossy dark green leaves.

2 Drawing Sheets

BACKGROUND OF THE INVENTION

The present Invention relates to a new and distinct cultivar of Ornithogalum plant, botanically known as *Ornithogalum hybrida*, and hereinafter referred to by the name 'Chesapeake Sunburst'.

The new Ornithogalum is a product of a planned breeding program conducted by the Inventors in Beltsville, Md. and Escondido, Calif. The objective of the breeding program was to create new freely-flowering interspecific Ornithogalum hybrids with unique and desirable flower colors.

The new Ornithogalum originated from a crossing of two unidentified seedling selections resulting from a cross made by the Inventors between the *Ornithogalum hybrida* cultivar Kewensis (*Ornithogalum thyrsoides*×*O. dubium*), not patented, with the *Ornithogalum hybrida* cultivar Sunshine (*Ornithogalum dubium* ×*O. multifolium*), not patented. The cultivar Chesapeake Sunburst was discovered and selected by the Inventors as a flowering plant within the progeny of the stated cross in a controlled environment in Beltsville, Md. in 1994.

Asexual reproduction of the new Ornithogalum by tissue culture in a controlled environment in a laboratory in Beltsville, Md., has shown that the unique features of this new Ornithogalum are stable and reproduced true to type in successive generations.

SUMMARY OF THE INVENTION

The cultivar 'Chesapeake Sunburst' has not been observed under all possible environmental conditions. The phenotype may vary somewhat with variations in environment such as temperature, daylength, light intensity, and water or nutritional status without, however, any variance in genotype.

The following traits have been repeatedly observed and are determined to be the unique characteristics of 'Chesapeake Sunburst'. These characteristics in combination distinguish 'Chesapeake Sunburst' as a new and distinct Ornithogalum:

1. Strong and upright scapes.
2. Dense corymbose racemes with numerous bright yellow-colored flowers.
3. Glossy dark green leaves.

In side-by-side comparisons conducted by the Inventors in Beltsville, Md., plants of the new Ornithogalum differ from plants of the cultivar Sunshine, in the following characteristics:

1. Plants of the new Ornithogalum have stronger scapes than plants of the cultivar Sunshine.
2. Plants of the new Ornithogalum have a denser (less open) flower display than plants of the cultivar Sunshine.
3. Plants of the new Ornithogalum have bright yellow-colored flowers whereas plants of the cultivar Sunshine have yellow-orange-colored flowers.

In side-by-side comparisons conducted by the Inventors in Beltsville, Md., plants of the new Ornithogalum differ from plants of the cultivar Kewensis, in the following characteristics:

1. Plants of the new Ornithogalum have longer leaves than plants of the cultivar Kewensis.
2. Plants of the new Ornithogalum have shorter scapes than plants of the cultivar Kewensis.
3. Plants of the new Ornithogalum have bright yellow-colored flowers whereas plants of the cultivar Kewensis have cream-colored flowers.

DESCRIPTION OF THE PHOTOGRAPHS

The accompanying colored photographs illustrate the overall appearance of the new Ornithogalum, showing the colors as true as it is reasonably possible to obtain in colored reproductions of this type. Colors in the photographs may differ slightly from the color values cited in the detailed botanical description which accurately describe the colors of the new Ornithogalum.

The photograph on the first sheet comprises a side perspective view of a typical flowering plant of 'Chesapeake Sunburst'.

The photograph on the second sheet comprises a close-up view of a typical flowering inflorescence of 'Chesapeake Sunburst'.

DETAILED BOTANICAL DESCRIPTION

In the following description, color references are made to The Royal Horticultural Society Colour Chart except where general terms of ordinary dictionary significance are used. The following observations and measurements describe plants grown in Beltsville, Md., under commercial practice in a glass-covered greenhouse. During the production of the plants, day temperatures ranged form 18 to 27° C and night temperatures ranged from 13 to 21° C. Measurements and numerical values represent averages for typical flowering plants. Plants used for the description and photograph were grown in 12.5-cm containers for about 20 to 25 weeks after planting rooted tissue-cultured plantlets in the fall.

Botanical classification: *Ornithogalum hybrida* cultivar Chesapeake Sunburst.

Parentage:

*Female and male parents.*—Unidentified seedling selections resulting from a cross between *Ornithogalum hybrida* cultivar Kewensis *Ornithogalum thyrsoides*×*O. dubium*), not patented, and *Ornithogalum hybrida* cultivar Sunshine (*Ornithogalum dubium*×*O. multifolium*), not patented.

Propagation:

*Type.*—Tissue culture.

*Time to initiate roots from tissue-cultured micro-cuttings.*—About 10 days at 24° C.

*Root description.*—Quantity: About 20 to 30 primary roots arising from bulb. Diameter: About 6 to 8 cm. Color: 159C.

*Bulb description.*—Appearance: Tunicate. Diameter: About 2.5 cm. Circumference: About 7 to 8 cm. Color: 161B.

Plant description:

*Plant form.*—Upright flowering potted plant; inverted triangle. Leaves basal with central flowering stem. Flowers arranged in dense corymbose racemes.

*Crop time.*—Usually about 20 to 25 weeks are required to produce finished flowering plants in 12.5-cm containers from rooted tissue-culture plantlets.

*Plant height.*—About 15 to 20 cm.

*Plant width.*—About 30 to 40 cm.

*Leaves.*—Arrangement: Simple; basal; rosette; sessile. Quantity of leaves per plant: About 4 to 8. Length: About 15 to 20 cm. Width: About 2 cm. Shape: Linear. Apex: Acute. Margin: Entire. Texture, upper and lower surfaces: Glabrous, smooth. Color: Young leaves, upper and lower surfaces: 144A. Mature leaves, upper and lower surfaces: 137A, glossy; venation, 137A. Leaf sheath: Length: About 1.5 cm. Width: About 1.5 cm. Color: 155B.

Flower description:

*Flowering habit.*—Inflorescences scapose with single flowers, 3-merous, arranged in dense corymbose racemes. Flowers not fragrant; flowers persistent.

*Natural flowering season.*—Plants flower during the spring.

*Flower longevity on the plant.*—About one month.

*Flower longevity as a cut flower.*—About 3 to 4 weeks.

*Inflorescence size.*—Length: About 15 cm. Width: About 5 cm.

*Flower buds.*—Length: About 1.2 to 1.5 cm. Diameter: About 8 to 10 mm. Shape: Ovoid. Color: 137A.

*Flowers.*—Quantity of flowers and flower buds per plant: About 30 to 40 per flowering stem; each bulb produces about 1 to 3 flowering stems. Shape: Circular. Diameter: About 3 cm. Depth (height): About 1.5 cm.

*Perianth.*—Quantity/arrangement: Three petals and three sepals per flower; imbricate; separate. Length: About 1.5 cm. Width: About 1 cm. Shape: Pyriform. Apex: Slightly acute. Margin: Entire. Texture, upper and lower surfaces: Smooth, waxy. Color: When opening, upper and lower surfaces: 9A. Fully opened, upper and lower surfaces: Apex and center, 9A; base, 152A; glossy.

*Scape.*—Angle: Erect. Strength: Strong. Length: About 10 cm. Diameter: About 5 mm. Texture: Glabrous. Color: 137A.

*Pedicles.*—Strength: Strong. Length: About 3 to 3.5 cm. Diameter: About 3 mm. Texture: Glabrous. Color: 137A.

*Flower bracts.*—Arrangement: Single, subtending the perianth. Length: About 2.5 cm. Width: About 1 cm. Shape: Cymbiformis. Color: 137A.

*Reproductive organs.*—Stamens: Quantity: Six. Anther shape: Oval. Anther length: About 3 to 5 mm. Anther color: 14B. Amount of pollen: Abundant. Pollen color: 14B. Pistils: Quantity: One. Length: About 6 to 8 mm. Stigma shape: Tri-sulcate. Stigma color: 166C. Style length: About 3 to 4 mm. Style color: 166C. Ovary color: 147A.

*Seed.*—Seed production has not been observed.

Disease resistance: Resistance to pathogens common to Ornithogalums has not been determined.

It is claimed:

1. A new and distinct cultivar of Ornithogalum plant named 'Chesapeake Sunburst', as illustrated and described.

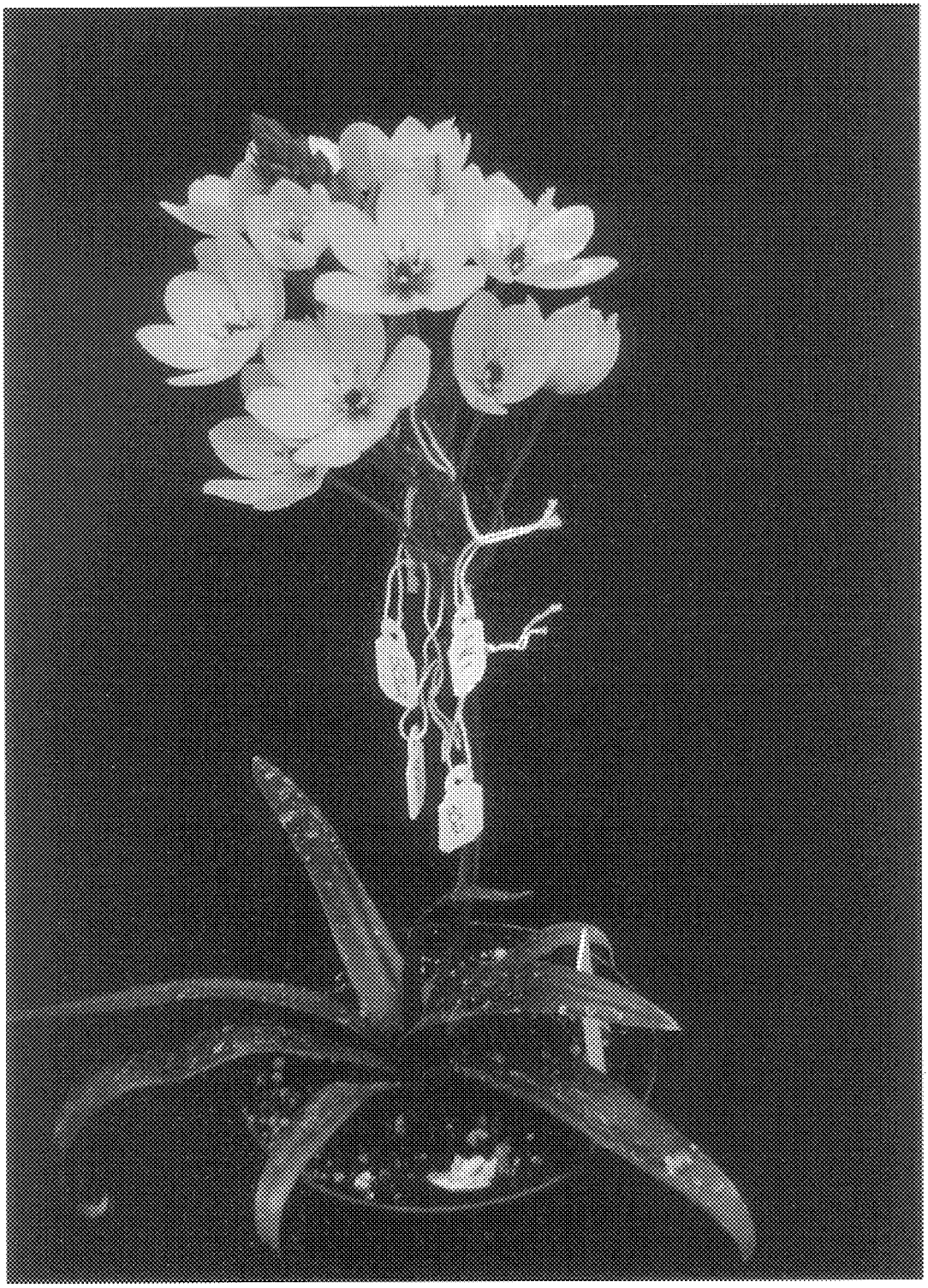

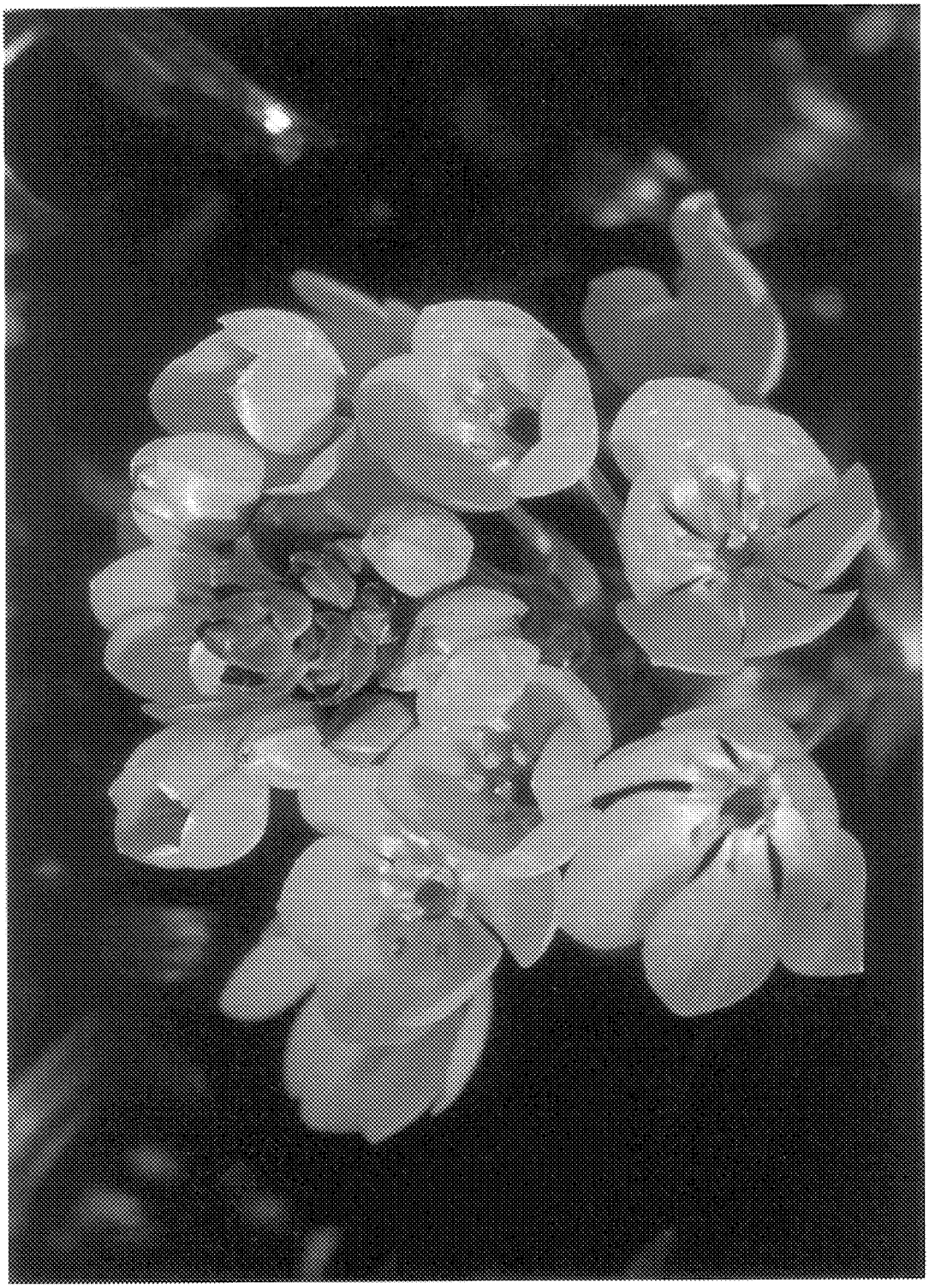

* * * * *